United States Patent [19]

Connor et al.

[11] 4,007,193
[45] Feb. 8, 1977

[54] SUBSTITUTED 3-(2-PYRIDINYL)-4(1H)-QUINOLINONE N-OXIDES

[75] Inventors: David T. Connor, Parsippany; Patricia A. Young, Madison; Maximilian von Strandtmann, Rockaway Township, all of N.J.

[73] Assignee: Warner-Lambert Company, Morris Plains, N.J.

[22] Filed: Sept. 8, 1975

[21] Appl. No.: 611,036

[52] U.S. Cl. .................. 260/288 CE; 260/283 SY; 424/258
[51] Int. Cl.² ....................................... C07D 401/04
[58] Field of Search .... 260/289 H, 288 C, 287 AN, 260/283 SY; 424/258

[56] References Cited
UNITED STATES PATENTS 3,753,993  8/1973  Lesher et al. ............... 260/287 AN Primary Examiner—Donald G. Daus
Assistant Examiner—David B. Springer
Attorney, Agent, or Firm—Albert H. Graddis; Frank S. Chow; Anne M. Kelly

[57] ABSTRACT

Substituted 3-(2-pyridinyl)-4-(1H)-quinolinone N-oxides having the formula I:

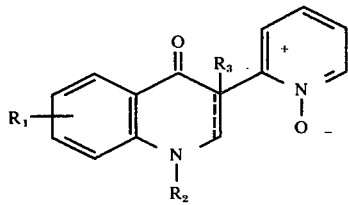

wherein $R_1$ is hydrogen, halogen, lower alkyl, hydroxy or alkoxy; $R_2$ is hydrogen or lower alkyl; $R_3$ is hydrogen or —CH$_2$OH; the dotted line indicates the possible presence of a double bond at the 2,3-position of the quinoline ring; the pharmaceutically acceptable acid addition salts thereof; and a process for the preparation thereof, are described. The compounds of the invention are useful for the treatment of hyperacidity and for the prevention of allergic and asthmatic reactions.

8 Claims, No Drawings

SUBSTITUTED 3-(2-PYRIDINYL)-4(1H)-QUINOLINONE N-OXIDES

DESCRIPTION OF THE PRIOR ART

Osborne et al., in J. Heterocyclic Chem. 1: 138–140 (1964), describe the preparation of 1-phenyl-2-(2-pyridinyl)ethanone N-oxide by the acylation of 2-picoline N-oxide, using sodium amide in liquid ammonia as the condensing agent. No pharmacological activity is reported for this or related compounds described by Osborne et al.

DESCRIPTION OF THE PARTICULAR EMBODIMENTS

This invention relates to substituted 3-(2-pyridinyl)-4(1H)-quinolinone N-oxides having the formula I:

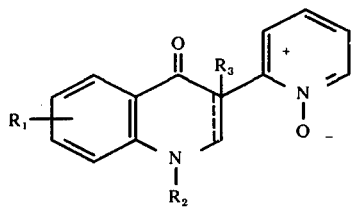

wherein $R_1$ is hydrogen, halogen, lower alkyl, hydroxy or alkoxy; $R_2$ is hydrogen or lower alkyl; $R_3$ is hydrogen or —$CH_2OH$; the dotted line indicates the possible presence of a double bond at the 2,3-position of the quinoline ring; and the pharmaceutically acceptable, acid addition salts thereof. Compounds of the formula I above wherein $R_1$ is hydrogen or halogen; $R_2$ is hydrogen or methyl; and $R_3$ is hydrogen or hydroxymethyl, as well as their pharmaceutically acceptable, acid addition salts, are particularly preferred.

The compounds of the invention having the formula II:

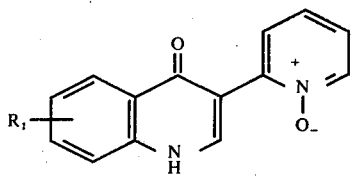

wherein $R_1$ is hydrogen, halogen, lower alkyl, hydroxy or alkoxy; are prepared by reacting a compound of the formula III:

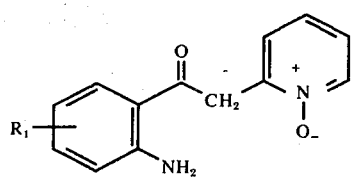

wherein $R_1$ is defined above in compound II, with a trialkylorthoformate, typically triethylorthoformate. The reaction is conducted in a suitable solvent such as pyridine and the like, in the presence of an organic base, typically piperidine or pyrrolidine.

The compounds of the invention having the formula IV:

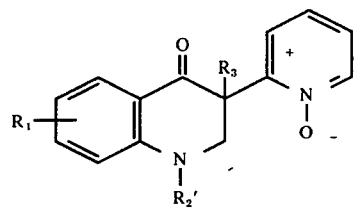

wherein $R_1$ is hydrogen, halogen, lower alkyl, hydroxy or alkoxy; $R_2'$ is lower alkyl; and $R_3$ is hydrogen or hydroxymethyl; are prepared by reacting a compound having the formula V:

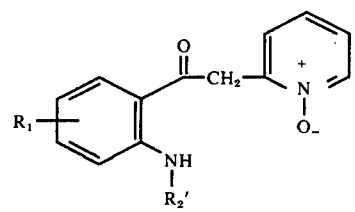

wherein $R_1$ and $R_2'$ are as defined above in compound IV, with either one or two moles of formaldehyde. If one mole of formaldehyde is used, one obtains a final product wherein $R_1$ and $R_2'$ are as defined above in compound IV, and $R_3$ is hydrogen. If two moles of formaldehyde are used, one obtains a final product wherein $R_1$ and $R_2'$ are as defined above in compound IV and $R_3$ is hydroxymethyl. The reaction is conducted in a suitable solvent, such as methanol and the like, in the presence of an organic base, typically piperidine or pyrrolidine.

The starting materials III and V used in preparing the compounds of this invention are prepared as described in co-pending U.S. Ser. No. 611,282, filed Sept. 8, 1975. Thus, compounds of the formula III and V are prepared by reacting an N-substituted isatoic anhydride having the formula VI:

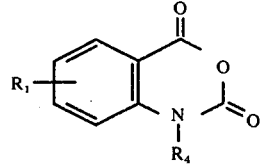

wherein $R_1$ is as defined above in compounds III and V and $R_4$ is hydrogen or lower alkyl, with a 2-picoline N-oxide of the formula VII:

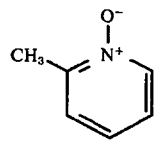

The above reaction is conducted in liquid ammonia in the presence of an alkali metal amide condensing agent such as sodium, potassium or lithium amide (sodium amide preferred).

Representative starting materials having the formulas III and V which may be prepared by the above-described reaction include: 1-[2-aminophenyl]-2-(2-pyridinyl)ethanone N-oxide, 1-[5-chloro-2(methylamino)phenyl]-2-(2-pyridinyl)ethanone N-oxide, 1-[5-methoxy-2-(methylamino)phenyl]-2-(2-pyridinyl)ethanone N-oxide, 1-[4-chloro-2-aminophenyl]-2-(2-pyridinyl)ethanone N-oxide, 1-[5-hydroxy-2-aminophenyl]-2-(2-pyridinyl)ethanone N-oxide, 1-[5-methyl-2-aminophenyl]-2-(2-pyridinyl)ethanone N-oxide, and 1-[3-methoxy-2-aminophenyl]-2-(2-pyridinyl)ethanone N-oxide.

Pharmaceutically acceptable acid addition salts of the compounds of this invention are prepared according to conventional procedures by treating the free base form of the compounds of the invention in an alcohol solution with the desired acid.

In the above formulas for the compounds of the invention, the R group definitions may be more fully described as follows: the term "lower alkyl" is meant to include lower aliphatic hydrocarbons having 1 to 7, preferably 1 to 4 carbon atoms in the alkyl chain, such as methyl, ethyl, propyl, isopropyl, butyl or isobutyl. This definition for lower alkyl also applies to the alkyl portions of "alkoxy". The term "halogen" is meant to include bromine, chlorine, iodine and fluorine.

The compounds of the invention having formula II:

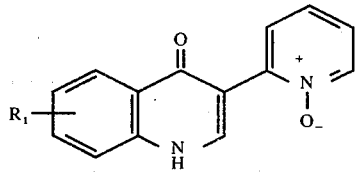

wherein $R_1$ is hydrogen, halogen, lower alkyl, hydroxy or alkoxy, exhibit gastric/anti-secretory activity when tested according to the procedure described by H. Shay et al., Gastroenterology 5: 43 (1945). In this last-mentioned test, male Long Evans Hooded rats (150–200 gms.) are fasted for 24 hours prior to testing (water ad lib). Rats are randomly divided into groups of 5 rats each and housed individually. At the time of testing, each rat is lightly anesthetised with ether, its stomach exposed through a midline abdominal incision and the pylorus ligated with silk thread. The incision is sutured, closed and covered with Flexible Collodion, U.S.P. to prevent ingestion of blood. Test compound or vehicle control is administered (a) intraduodenally prior to closing the incision; (b) intraperitoneally immediately after ligation; or (c) orally as a one hour pretreatment. Four hours later, the rats are sacrificed by ether and their stomachs removed and opened.

Gastric contents are placed in centrifuge tubes and centrifuged to remove debree. The volume of gastric juice is measured (expressed in milliliters) and titratable acidity determined electrometrically to pH 7.4 (expressed as milliequivalents of acid per liter). Results are expressed as percent reduction of volume and/or titratable acidity from control group average. Reduced gastric acid secretion in experimental animals in the above-described test is considered to be representative of pharmacological utility in the treatment of hyperacidity in humans.

Thus, the compounds of the invention are active in the treatment of hyperacidic conditions when administered to mammals at a dose level of from about 20 to about 50 mg/kg of body weight by the oral or parenteral route. This dosage may be varied depending on the severity of the condition, the age, weight, sex and class of mammal being treated, as well as the route of administration. For example, when 3-(2-pyridinyl)-4(1H)-quinolinone N-oxide (the compound of Example 1) is tested in the pylorus ligated rat in the above-described procedure at a dose of about 20 mg/kg, intraperitoneally, a reduction of about 55.2% in volume of gastric acid was obtained, compared to controls.

The compounds of the invention having formula IV:

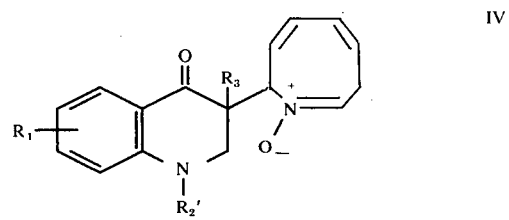

wherein $R_1$ is hydrogen, halogen, lower alkyl, hydroxy or alkoxy; $R_2'$ is lower alkyl and $R_3$ is hydrogen or hydroxymethyl, are active in prevention of allergic conditions (typically, asthmatic reactions) in mammals such as rats and guinea pigs as evidenced by positive results in the passive cutaneous anaphylaxis screen (PCA test). The PCA screen is a modification of the procedures described by I. Mota, Life Sciences, Vol. 4, No. 7: 465–474 (1963) and Z. Ovary and O. Bier, Proc. Soc. Exptl. Biol. Med., 81: 584–586 (1952) and provides a measure of the effectiveness of test compounds in inhibiting the release or action of toxic products arising from the combination of reaginic antibodies with specific antigens. These toxic products are causative factors in such disorders as bronchial allergic asthma (extrinsic reagins), exercise asthma, cold asthma, hay fever, perennial allergic rhinitis, food allergies, serum or drug allergies, insect sting allergies, angioneurotic edema, atopic dermatitis, including infantile eczema, urticaria, dermographism, dermatoconjunctivitis, acute allergic conjunctivitis, chronic allergic conjunctivitis and the like.

Inhibition of reaginic antigen/antibody reactions in experimental animals such as rats and guinea pigs is regarded as representative of inhibition of human reaginic antigen/antibody reactions which occur during allergic episodes.

In the PCA screen, rats are sensitized with 1 mg of ovalbumin (Pentex, Kankakee, Ill.) intramuscularly and with $10^{10}$ B. pertussis organisms (Parke-Davis and Co., Detroit, Michigan; Bio. 210) intraperitoneally. On the 14th day the animals are bled and the serum prepared in the usual manner. The reaginic nature of anti-ovalbumin serum thus obtained is verified by the use of standard criteria.

Passive cutaneous anaphylaxis is induced as described by Ovary and Bier (1952) and by Mota (1963). Suitable antibody concentration in 0.1 ml to result in reactions between 7 and 19 mm in diameter (usually 1:5 to 1:40 dilutions) are injected intradermally on either side of the dorsal midline of rats. Forty-eight hours later, the animals are dosed with drug and injected in the tail vein with 1 ml of saline containing 0.25% Evans blue and 1 mg ovalbumin. Thirty minutes later animals are sacrificed with ether, the dorsal skin reflected, and the mean orthogonal diameter of the reaction site measured.

A linear relationship can be shown to exist between the relative antibody concentration and the diameter of the resultant reaction if the antibody concentration is adjusted to yield diameters between approximately 7 and 19 mm. For each experiment, a line is fitted by the least squares method for the relationship of the diameter to the relative antibody concentration to derive the base-line diameter. The percentage inhibition due to drug treatment is then calculated by the formula:

$$\% \text{ inhibition} = \left[ 1 - \frac{(\text{diameter of experimental} - \text{base value})}{(\text{diameter of control} - \text{base value})} \right] \times 100$$

The significance of the inhibition is measured by Student's t-test.

For administration, the compounds are suspended by trituration in 1% gum tragacanth and 0.15M saline so as to give 10 ml/kg body weight.

Thus, the compounds of this invention are active for the inhibition of reagin-mediated allergic disorders when administered to mammals in need thereof at dose levels of from about 10 to about 25 mg/kg of body weight, by the oral or parenteral route. This dosage may be varied depending upon the severity of the condition, the age, weight, sex and class of mammal being treated, as well as the route of administration. For example, 2,3-dihydro-3-(hydroxymethyl)-1-methyl-3-(2-pyridinyl)-4(1H)-quinolinone N-oxide (the compound of Example 2) shows a 54% inhibition of the allergic response at 25 mg/kg when tested in a passive cutaneous anaphalaxis (PCA) screen, as described above. Consequently, the compounds of this invention are potentially useful in the treatment of asthma, hay fever and other allergic conditions.

In use, the compound of the invention may be combined with parenterally acceptable vehicles, such as gum tragacanth, in saline suspension, to provide dosage forms suitable for parenteral administration; or they may be combined with pharmaceutical diluents such as lactose, cornstarch, and the like and formulated into tablet or capsule dosage forms.

To further illustrate the practice of this invention, the following examples are included.

EXAMPLE 1

EXAMPLE 1

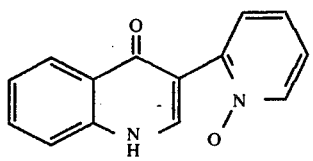

3-(2-Pyridinyl)-4(1H)-Quinolinone N-oxide

A solution of 1-[2-aminophenyl]-2-(2-pyridinyl)ethanone N-oxide (2.0 g), triethyl orthoformate (2.5 ml), pyridine (20 ml) and piperidine (15 drops) is refluxed under nitrogen for 20 hours. The product precipitates out. Recrystallization from N,N-dimethylformamide gives white crystals (0.9 g, 43%), m.p. dec 300° C.

Mass Spectrum
observed molecular ion: 238·0788
calculated for $C_{14}H_{10}N_2O_2$ 238·0742

EXAMPLE 2

EXAMPLE 2

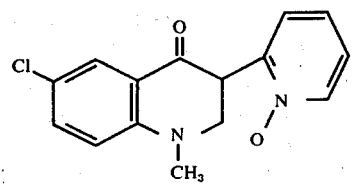

6-Chloro-2,3-Dihydro-1-Methyl-3-(2-Pyridinyl)-4(1H)-Quinolinone N-Oxide

A solution of 1-[5-chloro-2-(methylamino)phenyl]-2-(2-pyridinyl)ethanone N-oxide (15 g), 36% formaldehyde (0.9 m, 4.1 g), methanol (200 ml) and pyrrolidine (2 ml) is refluxed under nitrogen for 20 minutes. The solvents are removed under reduced pressure. Crystallized from isopropanol. Recrystallization from absolute ethanol gives bright yellow-green crystals (7.75 g, 49.5%), m.p. 135–37° C.

Anal. Calcd. for $C_{15}H_{13}ClN_2O_2$: C, 62.40; H, 4.54; N, 9.70; Cl, 12.28. Found: C, 62.28; H, 4.62; N, 9.67; Cl, 12.19.

EXAMPLE 3

EXAMPLE 3

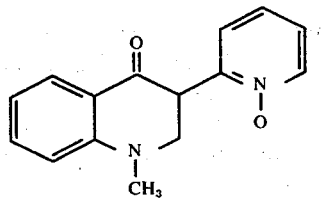

2,3-Dihydro-1-Methyl-3-(2-Pyridinyl)-4(1H)-Quinolinone N-Oxide

A solution of 1-[2-(methylamino)phenyl]-2-(2-pyridinyl)ethanone N-oxide (16.0 g), 36% formaldehyde (0.9 m, 4.96 g), methanol (100 ml) and pyrrolidine (4 ml) is refluxed under nitrogen for 50 minutes. The solvents are removed under reduced pressure. Crystallization from isopropanol gives yellow-green crystals (10.45 g, 62.2%), m.p. 132–34° C.

Anal. Calcd. for $C_{15}H_{14}N_2O_2$: C, 70.85; H, 5.55; N, 11.02. Found: C, 70.67; H, 5.63; N, 11.02.

EXAMPLE 4

EXAMPLE 4

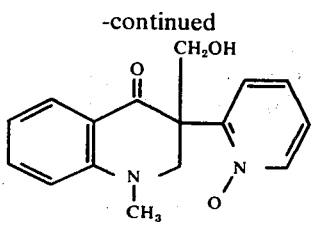

2,3-Dihydro-3-(Hydroxymethyl)-1-Methyl-3-(2-Pyridinyl)-4(1H)-Quinolinone N-Oxide A solution of 1-[2-(methylamino)phenyl]-2-(2-pyridinyl)ethanone N-oxide (15.0 g), 36% formaldehyde (41.0 g), methanol (150 ml) and pyrrolidine (2 ml) is refluxed under nitrogen for 30 hours. The product crystallized on cooling. Recrystallization from absolute ethanol gives green-yellow crystals (8.5 g, 50%), m.p. 198–200° C.

Anal. Calcd. for $C_{16}H_{16}N_2O_3$: C, 67.59; H, 5.67; N, 9.85. Found: C, 67.58; H, 5.69; N, 9.84.

We claim:

1. A compound of the formula IV:

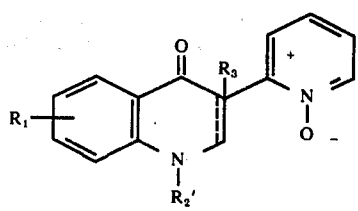

wherein $R_1$ is hydrogen, halogen, 1 to 7 carbon lower alkyl, hydroxy or 1 to 7 carbon lower alkoxy; $R_2$ is 1 to 7 lower alkyl; $R_3$ is hydrogen or hydroxymethyl; and the pharmaceutically acceptable acid addition salts thereof.

2. A compound of the formula IV according to claim 1 wherein $R_1$ is hydrogen or halogen; $R_2$ is methyl and $R_3$ is hydrogen or hydroxymethyl.

3. A compound according to claim 1 which is 6-chloro-2,3-dihydro-1-methyl-3-(2-pyridinyl)-4(1H)-quinolinone N-oxide.

4. A compound according to claim 1 which is 2,3-dihydro-3-(hydroxymethyl)-1-methyl-3-(2-pyridinyl)-4(1H)-quinolinone N-oxide.

5. A compound according to claim 1 which is 2,3-dihydro-1-methyl-3-(2-pyridinyl)-4(1H)-quinolinone N-oxide.

6. A process for preparing a compound having the formula IV:

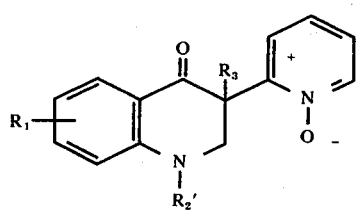

wherein $R_1$ is hydrogen, halogen, 1 to 7 carbon lower alkyl, hydroxy or 1 to 7 carbon lower alkoxy; $R_2$ is 1 to 7 carbon lower alkyl and $R_3$ is hydrogen or hydroxymethyl which comprises reacting a compound of the formula V:

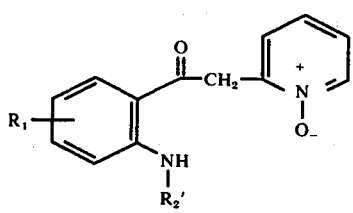

wherein $R_1$ and $R_2'$ are as defined above in compound IV with formaldehyde to effect ring closure, said compound V and formaldehyde being present in a mole ration of 1 to 1 to obtain the compound of formula IV wherein $R_3$ is hydrogen; and said formaldehyde being present in excess to obtain the compound of formula IV wherein $R_3$ is hydroxymethyl.

7. A process according to claim 6 wherein 1 mole of compound V is reacted with 1 mole of formaldehyde to obtain a compound having the formula IV wherein $R_3$ is hydrogen.

8. A process according to claim 6 wherein 1 mole of compound V is reacted with 2 moles of formaldehyde to obtain a compound having the formula IV wherein $R_3$ is hydroxymethyl.

* * * * *